(12) United States Patent
Fernandez Molina et al.

(10) Patent No.: US 7,776,342 B2
(45) Date of Patent: Aug. 17, 2010

(54) PREPARATIONS THAT POTENTIATE IMMUNOGENICITY IN LOW IMMUNOGENIC ANTIGENS

(75) Inventors: Luis Enrique Fernandez Molina, Havana (CU); Belinda Sanchez Ramirez, Havana (CU); Eduardo Raul Suarez Pestana, Havana (CU); Anabel de la Barrera Aira, Havana (CU); Circe Mesa Pardillo, Havana (CU); Joel de Leon Delgado, Havana (CU); Yildian Diaz Rodriguez, Havana (CU); Rolando Perez Rodriguez, Havana (CU)

(73) Assignee: Centro de Immunologia Molecular, Ciudad de la Havana (CU)

( * ) Notice: Subject to any disclaimer, the term of this patent is extended or adjusted under 35 U.S.C. 154(b) by 1187 days.

(21) Appl. No.: 10/003,463

(22) Filed: Dec. 6, 2001

(65) Prior Publication Data

US 2002/0136735 A1 Sep. 26, 2002

(30) Foreign Application Priority Data

Dec. 6, 2000 (CU) ........................... 285/00
Jul. 13, 2001 (CU) ........................... 167/01

(51) Int. Cl.
*A61K 39/095* (2006.01)
*A61K 39/00* (2006.01)

(52) U.S. Cl. ............... 424/249.1; 424/184.1; 424/277.1
(58) Field of Classification Search ................. 530/350; 424/450
See application file for complete search history.

(56) References Cited

U.S. PATENT DOCUMENTS

| 4,857,637 | A | * | 8/1989 | Hammonds et al. | ....... | 424/185.1 |
| 5,726,292 | A | * | 3/1998 | Lowell | ....... | 530/403 |
| 5,788,985 | A | * | 8/1998 | Rodriguez et al. | ....... | 424/277.1 |
| 6,149,921 | A | * | 11/2000 | Rodriguez et al. | ....... | 424/277.1 |

FOREIGN PATENT DOCUMENTS

| JP | 07-504683 A | 5/1995 |
| JP | 08-53366 A | 2/1996 |
| JP | 10-504323 T | 4/1998 |
| WO | 94/01133 A1 | 1/1994 |
| WO | 96/40116 A1 | 12/1996 |

OTHER PUBLICATIONS

Udayachander et al (Human Antibodies, 1997, 8:60-64).*
Carr et al (Melanoma Research, Jun. 2001, 11:219-227).*
Ramirez et al (Int J Cancer, 2006, 119:2190-2199).*
Estevez et al (Vaccine, Aug. 2000, 18:190-197).*
Livingston et al, Vaccine, 1993, 11:1199-1204.*
Levi et al (Vaccine, 1995, 13:1353-1359).*
Lowell et al (Science, 1988, 240:800-802).*
VanCott et al (J of Immunology, 1998, 160:2000-2012).*
Stedman's Medical Dictionary, p. 1, printed 2006.*
Robert J. Binder, et al., "CD91: a receptor for heat shock protein gp96", Nature Immunology, Aug. 2000, vol. 1, No. 2, pp. 151-155.
Marina Cella, et al., "Inflammatory stimuli induced accumulation of MHC class II complexes on dendritic cells", Nature, Aug. 1997, vol. 388, pp. 782-787.
Guo-Min Deng, et al., "Synovial cytokine mRNA expression during arthritis triggered by CpG motifs of bacterial DNA", Arthritis Research, 2001, vol. 3, pp. 48-53.
Genevieve De Becker, et al., "The adjuvant monophosphoryl lipid A increases the function of antigen-presenting cells", International Immunology, vol. 12, No. 6, pp. 807-815, 2000.
Francisco Estevez, et al., "Enhancement of the immune response to poorly immunogenic gangliosides after incorporation into very small size proteoliposomes (VSSP)", Vaccine, vol. 18, 2000, pp. 190-197.
Eric Hailman, et al., "Lipopolysaccharide (LPS)-binding Protein Accelerates the Binding of LPS to CD14", J. Exp. Med., The Rockefeller University Press, Jan. 1994, vol. 179, pp. 269-277.
G. Hartmann, et al., "CpG DNA: A potent signal for growth, activation, and maturation of human dendritic cells", Proc. Natl. Acad. Sci. USA, Immunology, Aug. 1999, vol. 96, pp. 9305-9310.
Hiroaki Hemmi, et al., "A Toll-like receptor recognizes bacterial DNA", Nature, vol. 408, Dec. 2000, pp. 740-745.

(Continued)

*Primary Examiner*—Laura B Goddard
(74) *Attorney, Agent, or Firm*—Rothwell, Figg, Ernst & Manbeck p.c.

(57) ABSTRACT

This invention discloses means for obtaining immunogenic peptides, polypeptides, proteins, and their corresponding nucleic acid sequences, target cells with vaccine interest, or lysates thereof, without making structural changes in said antigens, through their association with Very Small Size Proteoliposomes.

The object of the invention is to provide immunogenic compositions containing peptides, polypeptides, proteins, their corresponding DNA sequences, cells or their lysates and Very Small Size Proteoliposomes (VSSP), which are formed by binding the Outer Membrane Protein Complex (OMPC) of *Neisseria meningitidis* with gangliosides, by means of hydrophobic links. Additionally, it is stated that these compositions can be formulated alone or in the form of emulsions with the Incomplete Freund's Adjuvant (IFA), and may also be lyophilized.

The essence of the invention consists in describing compositions that triggers immunogenicity in low immunogenic antigens, such as growth factor receptors, without imparting structural changes therein. Particularly, this invention refers to preparation of immuno-stimulating compositions capable of generating antigen-specific immune responses, even in immuno-compromised hosts, such as those suffering form cancer or viral or bacterial chronic infections. In said patients, the administration of the vaccine compositions described in this invention has lead to the reestablishment of the functionality of the immune system. Vaccine compositions of this invention can be used to protect or treat infectious, or autoimmune diseases.

13 Claims, 5 Drawing Sheets

OTHER PUBLICATIONS

Pascale Jeannin, et al., "OmpA targets dendritic cells, induces their maturation and delivers antigen into the MHC class I presentation pathway", Nature Immunology, vol. 1, No. 6, Dec. 2000, pp. 502-509.

Isabelle Miconnet, et al., "Cancer Vaccine Design: A Novel Bacterial Adjuvant for Peptide-Specific CTL Induction", The Journal of Immunology, 2001, vol. 166, pp. 4612-4619.

Rolando Perez, et al., "Epidermal growth factor receptors in human breast cancer", Breast Cancer Research and Treatment, vol. 4, 1984, pp. 189-193.

Yasuaki Tamura, et al., "Immunotherapy of Tumors with Autologous Tumor-Derived Heat Shock Protein Preparations", Science, Oct. 1997, vol. 278, pp. 117-120.

Disis M.L., et al., "Peptide-Based, but Not Whole Protein, Vaccines Elicit Immunity to HER-2/neu, an Oncogenic Self-Protein," J. Immunol. 156:3151-3158 (1996), © 1996 by the American Association of Immunologies.

Harada, Y., et al., "Density of GM3 with Normal Primary Structure Determines Mouse Melanoma Antigenicity; a New Concept of Tumor Antigen," Jpn. J. Cancer Res., 80:988-992 (1989).

* cited by examiner

Specific recognition of immmunized mice sera.

Figure 3.

Cytolitic activity of mice immunized sera

PREPARATIONS THAT POTENTIATE IMMUNOGENICITY IN LOW IMMUNOGENIC ANTIGENS

TECHNICAL FIELD

This invention relates to human medicine, and specially to protective and/or therapeutic vaccines that confer protection against infectious, and auto-immune diseases, and cancer; and particularly provides vaccine compositions inducing or increasing an immune response to low immunogenic antigens.

PRIOR ART

The poor success achieved to date in preventing and treating a group of infectious diseases, cancer, and auto-immune diseases using vaccines is due to a combination of various factors. Mainly, the low immunogenicity of the relevant antigens, ignorance about how to manipulate the immune system regulation, and evasion strategies of pathogens and tumors, and the host immuno-suppression, inter alia.

In the state of the art, low immunogenic antigens are well-known to be those peptides, polypeptides, and proteins (or their corresponding DNA sequences) that are present in tumors and normal tissues, or associated to pathogens, which produce chronic infections by evading the action of the immune system.

Among low immunogenic antigens, growth factor receptors with kinase activity in tyrosine residues have shown to be closely related to the development of tumors, and tumor metastasis, and in some cases, they have shown to be valuable as indicators of a bad prognosis in cancer. This is the case for receptors like the Epidermal Growth Factor Receptor (EGF-R) also known as HER-1, the Epidermal Growth Factor Receptor 2 (HER-2), and the Platelets-Derived Growth Factor Receptor (PDGF-R).

The over-expression of these receptors in some kinds of neoplasia, mainly of epithelial origin, has been the target in cancer immuno-therapy. This is the case of breast, bladder, ovarian, vulva, colon, lung, brain, prostate, and head-neck tumors. The presence of EGF-R has proven to be an indication of a bad prognosis in breast cancer (Pérez R et al. 1984. Breast Cancer and Treatment 4:189-193). Even though the role of the EGF/EGF-R system in the regulation of tumor growth is yet not known, it has been suggested that the expression of the EGF-R in tumor cells provides a mechanism for autocrine stimulation, which leads to a disordered proliferation of said cells (Schlessinger J et al. (1983) Crit Rev Biochem 14 (2):93-111).

By reason of being highly expressed in tumors, the Epidermal Growth Factor Receptor has been the target of Passive Immuno-therapy (PI) with monoclonal antibodies in their native form, associated with drugs, toxins, or radioactive isotopes (Vollmar AM et al. (1987) J Cell Physiol 131:418-425). Several clinical trials with monoclonal antibodies (MAb) are in their way, and some of them have shown promissory results, that is the case of a clinical study with MAb C225 in breast cancer, pancreatic cells and renal cells in phase II and head-neck in phase III (Mendelsohn J et al. (1999) American Society of Clinical Oncology Meeting). Another Phase II clinical trial that showed good results is that performed for MAb IOR egf/r3 in head-neck tumors (Crombet T et al. (2000) Cancer Biotherapy and Biopharmaceutical, accepted manuscript).

On the other hand, the Specific Active Immuno-therapy (SAI) using EGF-R as a target, has never been developed by reason of its low immunogenicity as a self molecule, and its wide expression in the tissues, which has been an issue that has prevented immunologists from considering this option (Disis M L, and Cheever M A (1996) Current Opinion in Immunology 8:637-642). SAI has advantages over PI, since PI does not activate the specific cellular effector path of the immune response, and its effect depends on the half-life of such antibodies used, being generally necessary to practice continuous re-infusions in order to accomplish the desired effects.

To develop efficient vaccines, carriers and adjuvants must act to overcome the low immunogenicity of relevant antigens by means of an appropriate regulation of the immune system, and to jointly conspire against the evasion strategies of pathogens, and tumors. For this reason, the search of new carriers, and adjuvant systems currently constitutes an important research area.

In the last years, new theories and emergent knowledge about the immune system regulation have opened new experimentation fields to develop more efficient carriers, and adjuvants. Fearon, et al. (Science,Vol.272, pp 50-53, 1996) have taught that a protective immunity is the outcome of the interaction between two crucial systems: the innate immunity, and the acquired immunity. Cells responsible for acquired immunity cannot distinguish the structures requiring an immune response from those not requiring it, therefore they need to be instructed by the innate immune system cells. An essential link between the innate immunity, and the acquired immunity is provided by the Antigen-Presenting Cells (APC), among them Dendritic Cells (DC) are the most efficient inductors of the immune response, both primary, and secondary DCs. In particular, DCs are crucial because they are the only APCs capable of activating virgin T lymphocytes.

Molecules related to innate immunity have been recently identified, and they may be considered as a new generation of carriers, and adjuvants, because they are able to cause the DCs to mature, and mediate the cross-presentation of the antigens linked to them.

There is a series of works in this sense within the state of the art. Giroir, (Crit. Care Med., Vol.5, pp 780-789, 1993), Cella, et al. (Nature, Vol.388, pp 782-787. 1997) and Hailman, et al. (J. Exp. Med., Vol. (J. Exp. Med., Vol. 79, pp 269-277. 1994) teach that the interaction between the lipopolysaccharide (LPS) and the innate immunity recognition systems is the most potent of all, and stimulates the production of citokine and pro-inflammatory mediators in monocytes, macrophages, and neutrophils, thereby additionally increasing the expression of adhesion molecules. These inflammatory citokines are very important in the response to infections and tumors, but an excessive secretion of them leads to septic shock, which could be mortal for patients, and prevents the use of LPS as a vaccine adjuvant. The response is mediated by the complex formed between the LPS and a binding protein called Lipopolysaccharide-binding protein (LBP), which in turn interacts with the CD14 molecule. That molecule facilitates the interaction of the LPS with the signal molecules called Toll Receptors (TLR). Numerous evidences point to Toll Receptor 4 (TLR4) as the molecule of the Toll family involved in the transduction of the LPS signal.

Ulrich et al. (In Vaccine Design: The subunit and adjuvant approach p 495, edited by M F Powel and M J Newman, Plenum Press, New York 1995), Tholen, et al. (Vaccine, Vol.16, p 708. 1998), De Becker, et al. (Int. Immunol, Vol.12, pp 807-815. 2000) state out that there are non-toxic LPS derivatives, this is the case of the Monophosophoryl Lipid A (MPLA), which has adjuvant activity in cellular and humoral paths of the immune response, and has been administered to humans in several clinical trials. Even though it is set out that the MPLA maintains the LPS's immuno-stimulating properties, the authors have demonstrated that the MPLA induces migration, and functional maturation of the DCs in vivo, but at lower levels than those observed with the LPS.

Tamura, et al. (Science, Vol. 278, pp 117-120. 1997), and Binder, et al. (Nature Immunol., Vol. 1, pp 151-155. 2000) have reported that the Heat-Shock Proteins (HSP) are potent vehicles that stimulate cell immunity via the antigen cross-presentation phenomenon for their companion antigens. HSPs obtained from tumors have shown interesting anti-tumor effects in different models. Identification of CD91 as the receptor for HSP gp96 may reflect the presence of a specific capturing route of the HSP by the DCs, which has evolved to efficiently recruit peptides associated to antigens, infectious agents or damaged cells, and present them in the Major Histocompatibility Complex type I (MHC I). However, the use of HSP as vaccine carriers has the inconvenience of being obtained from the original source, for example, from tumors. This makes the procedure complicated and expensive, and it is never actually known which antigen was responsible for the effect.

Hartmann, et al. (Proc. Natl. Acad. Sci. USA, Vol. 96, pp 9305-9310. 1999), Hemmi, et al. (Nature, Vol. 6813, pp 740-5. 2000), Sparwasser, et al. (Eur. J. Immunol. Vol.12, pp 3591-3597. 2000), Hochreiter, et al. (Int. Arch. Allergy Immunol., Vol 124, pp 406-410. 2001), and Deng, et al. (Arthritis Res. Vol 3, pp 48-53. 2001) show that among molecules associated to innate immunity, identified as DC maturation inductors, the CpG sequences of bacterial DNA are found. It was recently demonstrated that cell response to the CpG sequences is mediated by TLR9, thereby indicating that this receptor is able to distinguish between bacterial DNA, and its own DNA. Induction of Cytotoxic T Lymphocytes (CTL) against different soluble antigens has been reproduced in genetically modified mice, negative to CD40, CD4 or MHC II markers. This leads to the conclusion that the CTL-activation being mediated by CpG occurs in the absence of help from CD4 T-cells, thereby conferring adjuvant properties to these kind of molecules. Nevertheless, the in vivo capacity of CpG sequences to deviate a response pattern from Th2 to Th1 is totally dependent on the antigen nature, and the immunization conditions, being this fact particularly valid when they are proteins. This may constitute an obstacle to the efficient use of CpG oligonucleotides as adjuvant, mainly in immuno-compromised hosts. It has also been described that bacterial CpG sequences may induce arthritis.

Jeannin, et al. (Nature Immunol., Vol. (Nature Immunol., Vol. 6, pp 502-509. 2000), and Miconnet, et al. (J. Immunol., Vol.166, pp 4612-4619. 2001) particularly found important immuno-stimulating properties in OmpA protein of *Klebsiella pneumoneae*, a Gram-negative bacteria. The experiments made with this protein expressed by recombinant techniques (kpOmpA), showed that the protein binds to, and induces complete DCs maturation using as signal molecule, that is TLR2 molecule. Another important property revealed by this protein is its capacity to lead antigens through the Class I presentation route, provided that this antigens are hydrophobically or covalently coupled. This is, in fact, its major limitation as vaccines carriers, since the covalent conjugation techniques have the inconvenience of producing chemical modifications both to the protein itself, and to the antigen, and the hydrophobic binding can only be used with the sub-group of hydrophobic antigens.

Lowell describes in U.S. Pat. No. 5,726,292, an immuno-potentiating system to increase the immunogenicity of peptides, polypeptides and proteins, which may be considered the nearest prototype to this invention. In the above-mentioned patent, the compositions are characterized by the antigens being chemically modified by means of the addition of at least one cysteine residue, and later conjugation with an aliphatic fatty acid or a hydrophobic peptide. Afterwards, the modified antigens are complexed with a proteosome by means of dialysis or a lyophilization process. Particularly, these compositions do not include glycosides.

DISCLOSURE OF THE INVENTION

The novelty of this invention consists in providing formulations that confer immunogenicity to peptides, polypeptides, proteins, and their corresponding DNA sequences, and target cells of vaccine interest, without the need of structural changes in said antigens, by means of their association with Very Small Size Proteoliposomes (VSSP) from *Neisseria meningitidis* bacteria, which carry therein innate immunity potent ligands, and gangliosides.

This invention shows that the immuno-potentiating carrier precisely consists of Very Small Size Proteoliposomes (VSSP) obtained from the association of the Outer Membrane Protein Complex (OMPC) from *Neisseria meningitidis*, Gram-negative bacteria, with gangliosides. This invention refers to formulations that are especially efficient when selecting low immunogenic antigens, and administering them to immuno-compromised hosts.

One object of this invention is to provide immunogenic compositions containing peptides, polypeptides, proteins, their corresponding DNA sequences, target cells or their lysates, as antigens, and Very Small Size Proteoliposomes (VSSP), which are formed binding the Outer Membrane Protein Complex (OMPC) from *Neisseria meningitidis* (Gram-negative bacteria) with gangliosides, by means of hydrophobic links. Additionally, it is stated that these compositions can be formulated alone or as emulsions with the Incomplete Freund's Adjuvant (IFA), and may also be lyophilized.

Another object of the invention is to provide immuno-stimulating compositions capable of generating antigen-specific immune responses, even in immuno-compromised hosts, such as individuals suffering from cancer or chronic viral infections. In said patients, the administration of the vaccine compositions described in this invention allows reestablishment of the functionality of the immune system.

Additionally, the vaccine compositions described in this invention constitute a solution to the growth factor receptor's immunogenicity problems, and their impact in the treatment of tumors, because said receptors showing tyrosine kinase activity, and the gangliosides which are specifically associated to them in membrane molecular clusters, are simultaneously presented to the host immune system in the context of the red flag signals contributed by the VSSP, and needed to effectively activate the dendritic cells (DC), and to produce the cross-presentation. These vaccine compositions obviate the use of protein conjugation chemical techniques, which generate new spurious immuno-dominant epitopes, further to the fact that they present its components to the immune system, mimicking the molecular associations in which they naturally occur in tumor cells.

On the other hand, this technological solution allows the use of the whole structure of the receptors, thereby solving the problem of immuno-dominance genetic restriction, contrary to other solutions that use derivative peptides, and that may present more limitations in this regard.

More specifically, the invention provides vaccine compositions for treating cancer. Said vaccine compositions contain as active ingredient one or more growth factor receptors or their extra-cellular domains, containing or not their transmembrane domains, and as a vaccine carrier, a Very Small Size Proteoliposomes (VSSP) derived from the *Neisseria meningitidis* external membrane protein complex, and the gangliosides that are specifically associated thereto, thereby forming membrane molecular clusters. Said vaccine compositions may additionally contain an appropriate adjuvant.

The vaccine compositions of the invention may be used in active immuno-therapy, specifically in tumors such as prostate, colon, lung, breast, ovary, head-neck, vulva, and bladder cancer, glioma, as well as in non-transmissible chronic diseases.

DETAILED DESCRIPTION OF THE INVENTION

This invention relates to pharmaceutical compositions able to potentiate immunogenicity in low immunogenic antigens, comprising:
 (A) one or more low immunogenic antigens;
 (B) a vaccine carrier consisting in proteoliposomes derived from the external membrane protein complex of a Gram-negative bacteria strain, and carrying gangliosides therein; and
 (C) eventually one or more adjuvants.

The compositions of this invention potentiate the immunogenicity of low immunogenic antigens, which may be peptides, polypeptides, proteins, and their corresponding nucleic acids sequences, as well as target cells of vaccine interest, or their lysates, and combinations thereof.

Within the low immunogenic antigens, the growth factor receptors or their extra-cellular domains may be used. Said growth factor receptors' extra-cellular domains may or may not contain their trans-membrane region.

The growth factor receptors that may be used to increase the immunogenicity are HER-1, HER-2, PDGF-R or any variation thereof containing the extra-cellular domain, in the absence or presence of their trans-membrane region.

Proteoliposomes for the vaccine carrier used in this invention are obtained from the Outer Membrane Protein Complex (OMPC) of a Gram-negative bacteria strain, preferably *Neisseria meningitidis*, which may be a wild type or a genetically modified strain.

In the compositions of the invention, the proteoliposomes carrying gangliosides therein are obtained by hydrophobically incorporating said gangliosides into the Outer Membrane Protein Complex (OMPC) of *Neisseria meningitidis*. GM1, and GM3 gangliosides, or their N-glycolylated variations may be used for this purpose.

The compositions of the invention additionally contain an adjuvant that may be an oily adjuvant or a natural or recombinant polypeptide.

The preferred oil adjuvant is the Incomplete Freund's Adjuvant or Montanide ISA 51. Likewise, when a polypeptide adjuvant is used it may be a cytosine, such as the granulocyte-macrophage colony stimulating factor, or a chymosin.

The compositions of this invention may be useful in the prevention, and treatment of cancer, particularly in prostate, colon, lung, breast, ovary, head-neck, vulva, and bladder cancer and glioma, as well as in non-transmissible chronic diseases.

Likewise, they may be used in the prevention and treatment of viral, and bacterial infectious diseases, and amongst them, it may be used in the treatment for Acquired Immuno-deficiency Syndrome, as well as in the treatment of auto-immune diseases.

This invention provides formulations that confer immunogenicity to low immunogenic peptides, recombinant or natural proteins, cellular lysates, intact cells and nucleic acids. The immuno-stimulating formulations can be defined as formulations having the capacity of stimulating both the humoral and the cell responses against a particular antigen. Furthermore, these formulations have the peculiar characteristic of reestablishing the immunity in immuno-compromised individuals, such as those suffering from cancer, and chronic viral infections or a specific type of auto-immune disease.

This invention describes that the immuno-potentiating carrier consists of Very Small Size Proteoliposomes (VSSP) obtained from the association of the Outer Membrane Protein Complex (OMPC) from the Gram-negative bacteria strain, *Neisseria meningitidis*, with gangliosides incorporated therein. The OMPC components are subjected to a dialysis process that lasts between 2 and 15 days, by means of which glycolylated and/or acetylated gangliosides are incorporated. A non-vesicular preparation is obtained as a result of the incorporation of gangliosides into the outer membrane complex; the resulting non-vesicular preparation is of very small molecular size, invisible to electronic microscope, soluble and showing high floatability.

The VSSPs of this invention show surprising immunological properties such as a dramatic ability to cause the dendritic cells to mature, and to immuno-reestablish immuno-suppressed patients. The VSSPs are obtained according to the specification of Cuban Patents 131/93 and 130/97, U.S. Pat. Nos. 5,788,985 and 6,149,921, as well as Estevez, et al. published article. (Vaccine, Vol. 18, pp 190-197. 1999).

The antigenic peptides used in this invention may be synthetic or be extracted from several sources. The preferred size of peptides may be between 7 and 25 amino acids, depending on the T cell type that is going to be stimulated. Nevertheless, the length may vary between 3 and 50 amino acids. The peptides may be neutral or may be positively or negatively charged. The hydrophobic nature of the peptides may also vary.

In the same way, the present invention reveals that the recombinant proteins used herein can be expressed in different expression systems, such as bacteria, yeast, plants, and mammalian cells. A preferred embodiment of this invention claims the use of *N. meningitidis* as expression system, wherein the proteins of interest are expressed at the external membrane of the bacteria itself. This makes possible that the protein of interest directly constitutes part of the OMPC. In this case, the expression of the whole protein is equally valid, or the insertion of some of its polypeptides or peptides into one or more of the links of the Outer Membrane Protein from *Neisseria meningitidis*, such as TBP, Opa, Opc, and P1, P2 and P3 porines.

Particular embodiments of this invention show that antigens from these vaccine compositions may be growth factor receptors having tyrosine kinase activity, which are overexpressed in tumor tissues, and alternatively, their extra-cellular domains, with or without trans-membrane region, and they have a specific relationship with gangliosides expressed in the tumor cell membrane. This is the case of HER-1, HER-2, and the PDGF receptor, among others.

The growth factor receptors to which this invention refers, are proteins obtained in mammalian cell expression plasmids by recombinant techniques, and Polymerase Chain Reaction (PCR) following the typical procedures described in Molecular Biology publications (Sambrook J, Fritsch E. F, Maniatis T, *Molecular Cloning* A Laboratory Manual, second edition, Cold Spring Harbor Laboratory Press, 1989). Plasmids containing these genes and encoding the receptors or variations thereof are steady transfected in mammalian cells, such as HEK 293 (ATCC CRL 1573), NIH-3T3 (ATCC CRL 1658), and CHO. The receptors or variations thereof are expressed at the membranes of the transfected lines, or are secreted into the supernatant, whatever the case may be.

These antigens are extracted from the mammalian cell membrane expressing it, or from the cell culture supernatant, and purified by chromatography. Then, they are filtered under sterile conditions, and lyophilized. They are left preserved at 4° C. The optimum quantities of these antigens in the vaccine formulations range between 1 µg to 1000 µg per dose.

For this particular type of antigens, the VSSP used in vaccine formulations contain gangliosides which are selected from those specifically associated to the growth factor receptors, such as GM3, and GM1, among others, forming membrane molecular clusters. VSSP are found in this vaccine composition in a range of 1 µg to 1000 µg based on the gangliosides amount per vaccine dose.

The preferred vaccine compositions of this invention containing growth factor receptors as antigens, for which immunogenicity is to be increased, may be prepared in different ways:
a) A given amount of VSSP solutions is added to the lyophilized growth factor receptors or their extra-cellular domains (containing or not the trans-membrane region) (1-100 mg of protein), such that the receptor/ganglioside mass ratio is in the range of between 0.1/1 to 1/1. The mixture is stirred at 4° C.-20° C., for a period of time between 5 minutes and 24 hours. This preparation is preserved at a temperature of 4° C. until it is administering to the host.

Just before administering it to the host, the aforementioned preparation is added to IFA at a volume/volume ratio between 40/60 and 60/40, and stirred for 10 to 30 minutes, at room temperature. The volume ratios cover the adequate range for the desired type of emulsion according to the inoculation route to be used.

Another equally convenient way of proceeding consists in keeping separate containers for the lyophilized growth factor receptors or the extra-cellular domains thereof (containing or not the trans-membrane region), and for the VSSP solutions preserved at 4° C. A given amount of VSSP solution is added to the growth factor receptors just before administration to the host; the vaccine composition is then prepared in the same manner as described in item a). c) A third way of proceeding consists in combining more than one growth factor receptor or its extra-cellular domain (containing or not the trans-membrane region) with the corresponding VSSP solutions in the vaccine composition. The amount of each antigen in the vaccine composition, and the ratios among them, will be within the range of 1 µg to 1000 µg per vaccine dose. Likewise, the amount of each ganglioside in the VSSP in the vaccine composition will be in the range of 1 µg to 1000 µg per vaccine dose.

In order to prepare the combined vaccine, the growth factor receptors or their extra-cellular domains (containing or not the trans-membrane region) that will be part of it, are lyophilized in the aforementioned amounts as per the corresponding item. Subsequently, a given amounts of VSSP solution is added, such that the receptor/ganglioside mass ratio is in the range of 0.1/1 to 1/1. Then, the mixture is stirred at 4° C.-20° C., for 5 minutes to 24 hours. This preparation is preserved at a temperature of 4° C. until it is administered to the host. Just before administering it to the host, the aforementioned preparation is mixed, by agitation, with IFA in a volume/volume ratio between 40/60 and 60/40, for 10 to 30 minutes, at room temperature. These volume ratios cover the appropriate range for the desired type of emulsion, according to the inoculation route to be used.
d) Another way of preparing the combined vaccine mentioned in item c) is as per the method referred to in item b).

On the other hand, the multi-antigenic systems, by being cells taken from established tumor lines or directly obtained from cancer patients, they are also used in the formulations of this invention. The cell inactivation is accomplished by means of gamma radiation therapy or treatment with Mitomycin C. Another equally convenient alternative is the use of oncolysates obtained by mechanic rupture or by virus infection of the tumor cells.

The immuno-potentiating preparations of this invention can be advantageously used in DNA and RNA vaccines. The immunogenicity of retro- and adenoviral vectors used as vaccine carriers, also increases when combining them with the described preparations of the invention. These vectors contain the genes encoding the subject antigenic proteins.

Usually, different immunogenic formulations are obtained when combining different antigen systems with the previously obtained VSSP. The antigens which are directly introduced by a recombinant technique into the outer membrane of N. meningitidis, and those which are incorporated into the proteoliposomes during the dialysis process, are already incorporated at the end of the VSSP elaboration process. Nevertheless, said modified proteoliposomes may also be used with other not incorporated antigens. This allows the preparations of multivalent vaccines.

The proteic antigen preparations are obtained by mixing 10 to 1000 µg of the antigenic peptide or protein with given amounts of VSSP, such that the total mass ratio of protein/ganglioside is in the range of 1 to 3. The preparations are preserved at a temperature of 4° C. until the administration to the host. Another equally convenient way of proceeding consists in separately preserving the antigenic solutions, and the VSSP solutions, at 4° C., and mixing them just before administration.

Formulations with nucleic acids are obtained by directly mixing the VSSP with the DNA or RNA solutions. The mixing process is carried out at 4° C. using 2-100 µg of nucleic acid per 0.1 mg of ganglioside in the VSSP. This method is feasible due to the absence of nucleases in the VSSP preparations.

In a particularly advantageous procedure shown in this invention, live viral vectors (Vaccinia, Fowlpox, or other virus) containing the DNA sequences of the proteins of interest, are administered to the host IV (intravenously), in amounts ranging from $10^6$ to $5\times10^7$ pfu. VSSPs are administered by intramuscular, subcutaneous, intradermal, oral or intranasal route, within 12 hours before, and 12 hours after administering the viral vector.

Preparations with the target cells of interest or their lysates are obtained by first precipitating the respective cultures by centrifugation, and then re-suspending the cellular precipitate in given amounts of VSSP such that the are $10^3$ to $5\times10^6$ cells per 0.1 mg of ganglioside. Said amounts are directly mixed by agitation, at 4° C.-20° C., for 5 to 24 hours. The preparations are preserved at a temperature of 4° C. until administration to the host.

Another equally convenient way of proceeding consists in keeping separately the cell suspensions or the corresponding lysates thereof, and the VSSP solutions, at 4° C., and mixing them together just before administration.

The preparations described in this invention, where antigens are mixed with or incorporated into the VSSP, may be administered alone or as an emulsion with the Incomplete Freund's Adjuvant (IFA). The emulsions are prepared just before being administered to the host. Each preparation is mixed by agitation with the adjuvant in a volume/volume ratio in the range of 40/60 to 60/40, for 10 to 30 minutes, at room temperature. Said volume ratio range covers the adequate range for the desired type of emulsion according to the inoculation route to be used.

In another preferred embodiment of this invention, the described preparations wherein the antigens are mixed or incorporated to the VSSP, are lyophilized before being administered either alone or as an emulsion with the Incomplete Freund's Adjuvant (IFA).

Vaccine compositions of this invention can be administered to the patient by parenteral routes (intramuscular, intradermal, subcutaneous) or by direct application to mucous membranes.

EXAMPLES

Example 1

Obtaining an Antigen of the Vaccine Composition Consisting in the Extra-cellular Domain (ECD) of Murine EGF-R (ECD-mEGF-R).

The gene encoding ECD-mEGF-R was amplified using the PCR technique, from complementary DNA (cDNA) from mouse liver. PCR was carried out by mixing 1 μg of cDNA with 10 pmoles of each specific primer. Later on, 0.2 mM of each dNTP and 1 U of Taq Polymerase were added. A total of 30 PCR cycles were performed: 9° C., 1 min (except for the first cycle which lasted 3 min); 56° C., 1 min; 72° C., 1 min, and 30 seconds (except for the last cycle which lasted 5 min.). The amplified gene was cloned in the mammalian cell expression vector pcDNA3 (Amp$^r$, f'ori, ColE ori, CMV-Promoter, SV40 ori, SV40pa, Neomycin, Invitrogen), and later on, the HEK-293 cell line was steady transfected with this plasmid. Transfection was carried out by conventional means, and the cells were grown in a selective medium. ECD-mEGF-R is obtained from the supernatant of the HEK-293/ECD-mEGF-R line that steady expresses the ECD-mEGF-R.

The ECD-mEGF-R obtained in the supernatant of the culture is purified by affinity chromatography techniques by coupling the ligand to the matrix (*Affinity Chromatography Principles and Methods* 3:12, Pharmacia fine Chemicals); thereafter it is filter sterilized and lyophilized.

Example 2

Obtaining a Vaccine Composition Comprising ECD-mEGF-R, VSSP-GM3, and Incomplete Freund's Adjuvant (IFA), and Combining all the Components Just Before Administration.

Proteoliposomes derived from the Outer Membrane Protein Complex (OMPC) from *Neisseria meningitidis* containing the incorporated GM3 ganglioside were obtained as described in the U.S. Pat. No. 6,149,921.

The OMPC complex from *N. meningitidis* used for this purpose was supplied by the "Carlos J. Finlay" Institute (C. Campa et al. EP 301992). 10 mg of this OMPC complex were dispersed in a 0.5 % sodium deoxycholate solution, and 0.1 % sodium dodecyl sulfate solution, additionally containing 10 mg of NGcGM3, by gentle mixing overnight at 4° C.

Separation of the soluble OMPC-NGcGM3 from the detergents was performed by dialysis, during 14 days, using a 3.5 KDa membrane.

The dialysate was ultracentrifuged at 100,000 g for one hour, and the immunogenic complex present in the supernatant was filter sterilized.

The extent of incorporation of the ganglioside into the protein was determined using the Bio-Rad reagent for proteins, and resorcinol for sialic acid. This way, an incorporation of 1 mg of NGcGM3 per mg of OMPC was obtained.

The amount of vaccine carrier as previously prepared was 120 μg based on the amount of gangliosides incorporated into the proteoliposomes per vaccine dose.

In order to prepare the immunogenic material, 1 mg of ECD-mEGF-R was lyophilized, and preserved at 4° C. until immunization. Just before administering to mice, 2.4 mg of VSSP-GM3 were added to the antigen (based on the ganglioside amount) in a 1 ml volume, and both components were mixed at room temperature for 15 minutes. Then 1 ml of IFA was added, and mixed by agitation at room temperature for 20 minutes.

Example 3

Obtaining a Vaccine Composition Comprising the ECD-mEGF-R, VSSP-GM3, and IFA, by Combining Part of the Components, and Preserving the Mixture Until Administration.

Proteoliposomes derived from the Outer Membrane Protein Complex (OMPC) from *Neisseria meningitidis* containing the incorporated GM3 ganglioside, were obtained as described in the U.S. Pat. No. 6,149,921. The amount of vaccine carrier used was 120 μg based on the amount of incorporated gangliosides per vaccine dose.

In order to prepare the immunogenic material, 1 mg of ECD-mEGF-R was lyophilized, and then 2.4 mg of VSSP-GM3 were added (based on the amount of incorporated gangliosides), in a volume of 1 ml. Both components were mixed at room temperature for 15 minutes, and the mixture was preserved at 4° C. until immunization. Just before administering to mice, 1 ml of IFA was added, and mixed by agitation at room temperature for 20 minutes.

Example 4

Obtaining a Combined Vaccine Comprising ECD-HER-1, ECD-HER-2, VSSP-GM3, and IFA.

Proteoliposomes derived from the Outer Membrane Protein Complex from *Neisseria meningitidis* containing the incorporated GM3 ganglioside were obtained as described in the U.S. Pat. No. 6,149,921. The amount of vaccine carrier used was 120 μg based on the amount of gangliosides incorporated into the proteoliposomes per vaccine dose.

In order to prepare the immunogenic material, 1 mg of ECD-HER-1, and 1 mg of ECD-HER-2 were lyophilized together, and preserved at 4° C. until immunization. Just before administering to mice, 2.4 mg of VSSP-GM3 were added (based on the amount of ganglioside) in a volume of 1 ml. All components were mixed at room temperature for 15 minutes. Then, 1 ml of IFA was added, and mixed by agitation at room temperature for 20 minutes.

Example 5

Induction of a Specific Immune Response Against Autologous EGF-R by Means of the Vaccine Composition.

C57BL/6 strain mice were immunized with the vaccine composition containing ECD-mEGF-R/VSSP-GM3, and IFA, prepared as described in Example 2. The immunogenic material dose was 50 μg per mice based on the amount of antigen in the composition. The immunization scheme consisted in three doses administered intramuscular (i.m.) every fifteen days, with blood extractions in the days 0, 21, 35 and 56 after the first immunization (Group II). As a reference group, mice from the same strain were immunized with 50 μg of the ECD-mEGF-R chemically conjugated with KLH, and adjuvanted in Complete Freund's Adjuvant (CFA), and IFA, was used, following the same immunization scheme (Group I). Obtained sera were analyzed by ELISA techniques for detection of ECD-mEGF-R. ELISA was carried out by coating the plate with 10 μg/ml of ECD-mEGF-R. After blocking the plate with PBS/5% calf serum, the sera from control, and immunized animals were incubated at different serial dilutions. Next, a mouse anti-IgG antibodies (specific for Fc) conjugated with alkaline phosphatase (Sigma) was added. All the aforementioned incubations were left 1 hour at 37° C., and after each of the mentioned steps three washes with PBS/0.05% Tween 20 were carried out. The reaction was developed with the addition of 1 mg/ml of substrate (p-nitrophenylphosphate) in diethanolamine buffer, pH 9.8. Absorbance at 405 nm was measured in an ELISA reader after 30 minutes.

100% of the mice immunized with the vaccine composition of the invention evoked an antibody response being specific against ECD-mEGF-R; the response was stronger during the immunization course, and reached antibody titres of up to 1/160000, while pre-immune sera did not recognize the ECD-mEGF-R. The isotype of the antibodies response was basically an IgG type.

Figure 1:
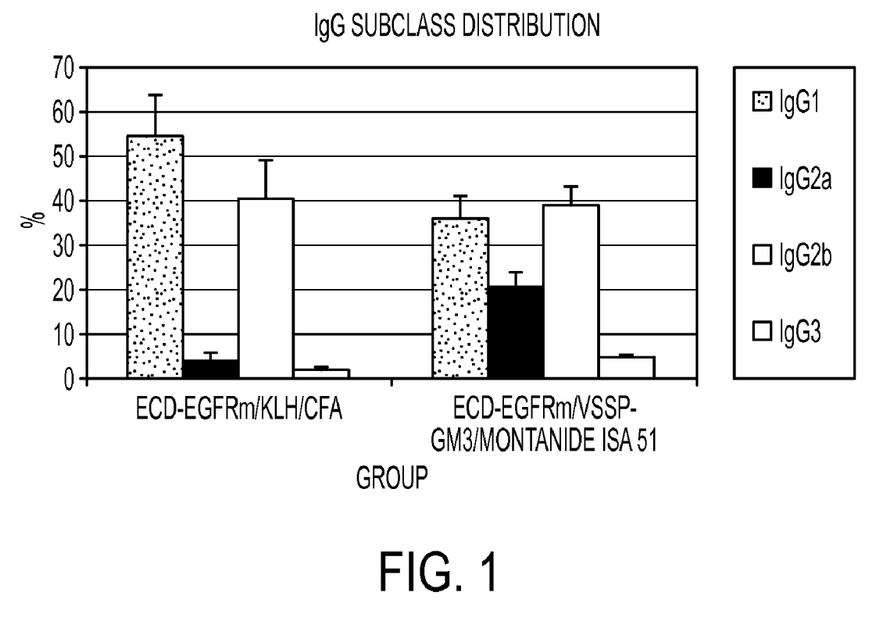
FIG. 1. Sub-class distribution of the induced antibodies as a result of immunization with ECD-mEGF-R/VSSP-GM3/IFA.

The subclass distribution of the induced antibody response was determined by ELISA. 20.21% of antibodies were IgG2a, 36.03% IgG1 and 38.93% were IgG2b, estimating a shift towards the Th1 response pattern in comparison with the control group (FIG. 1).

Although this vaccine composition is compared to a composition where ECD-mEGF-R is chemically bound to KLH, and wherein CFA is used as adjuvant, the induced antibody titres for the preparations are higher, and the sub-class distribution trend is that of a Th1 pattern, being favorable for said vaccine efficiency.

Mice immunized with ECD-mEGF-R/VSSP-GM3/IFA did not show clinical toxicity signs, and the biochemical tests performed on sera from said animals did not show differences to those of non-immunized animals (Table 1).

Example 6

Recognition of Sera From Mice Immunized with ECD-HER-1/VSSP-GM3/IFA to Cells Expressing the Human EGF-R.

A431 cell line (10000 cells/well) expressing the human Epidermal Growth Factor Receptor were incubated with pre-immune C57B/L6 mice serum diluted to 1/5 (A); monoclonal antibody ior egf-r3 against EGF-R as positive control in a concentration of 10 μg/ml (B); and immunized C57BL/6 mice sera diluted to 1/5 (C), for 30 minutes at room temperature.

Figure 2:
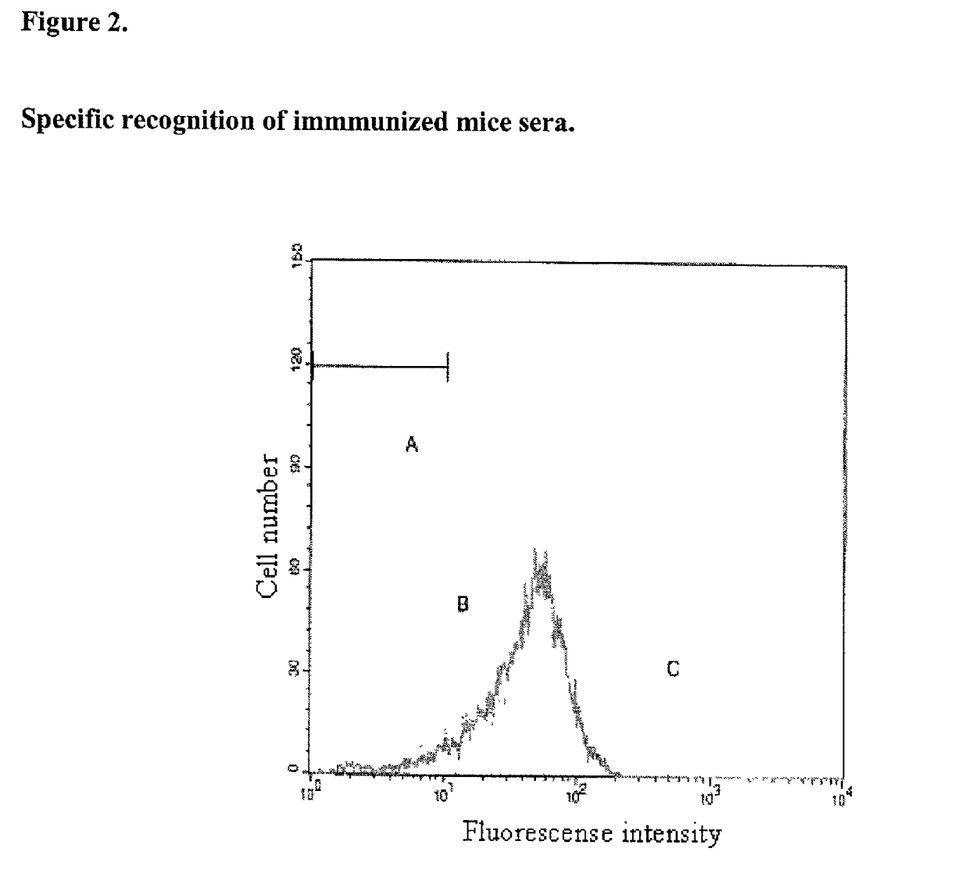
FIG. 2. Recognition of sera from mice immunized with ECD-HER-1/VSSP-GM3/IFA by cells expressing EGF-R.

Washings with a phosphate buffer/0.5% calf serum solution removed the excess of antibodies not bound to the receptor or bound thereto in a non-specific manner. Immuno-detection of the cells was performed by incubating the cells with a second anti-mouse antibody conjugated to fluorescein isothiocyanate diluted to 1/50, for 30 minutes at room temperature. The fluorescence intensity was measured in a flow cytometer (FC). Sera from mice immunized with the vaccine preparation recognized cells expressing the EGF-R with intensity comparable to that of the experimental positive control, in contrast to the pre-immune sera from the same animals (FIG. 2).

Example 7

Cytolytic Activity of Sera from ECD-HER-1/VSSP-GM3/IFA Immunized Mice

A431 cell lines ($3 \times 10^6$ cells) were incubated with radioactive sodium chromate $^{51}$Cr for 1 hour, and washing three times with culture medium eliminated the radioactive salts excess. The cells loaded with $^{51}$Cr were incubated with:

i) 50 μg/ml of monoclonal antibody ior-t3 (MAb against CD3, as negative control)

ii) 50 μg/ml of monoclonal antibody ior egf-r3 (MAb against EGF-R, as positive control)

iii) pre-immune C57BL/6 mice serum diluted to 1/20 iv) sera from C57BL/6 mice immunized with ECD-HER-1/VSSP-GM3/IFA diluted to 1/20.

After 1 hour of incubation at 37° C., 40 μl of rabbit complement were added allowing incubation at 37° C. Later on, the tubes were centrifuged, and 100 μl of the supernatant were used to measure in a gamma counter the release of $^{51}$Cr, as a measure of cellular lysis, mediated by the antibodies and the complement. The total incorporation was measured by means of total lysis with detergent.

TABLE 1

| Groups | Responder Animals | IgG Titers | | | | | | |
|---|---|---|---|---|---|---|---|---|
| | Day 21 | 1/100 | 1/500 | 1/1000 | 1/2500 | 1/5000 | 1/10000 | 1/20000 |
| I | 8/10 | 1 | 3 | 1 | | 1 | 1 | 1 |
| II | 10/10 | | 1 | 1 | 2 | 5 | 1 | |
| | Day 35 | 1/100 | 1/1000 | 1/2500 | 1/5000 | 1/10000 | 1/20000 | 1/40000 |
| I | 10/10 | | 2 | | 2 | 1 | | 5 |
| II | 10/10 | | 1 | | | 2 | 1 | 6 |
| | Day 56 | 1/1000 | 1/5000 | 1/10000 | 1/20000 | 1/40000 | 1/80000 | 1/160000 |
| I | 10/10 | 1 | 1 | 1 | 2 | 1 | 4 | |
| II | 10/10 | | 1 | | 1 | 2 | 4 | 2 |

Group I - Animals immunized with ECD-mEGF-R/KLH/CFA and IFA
Group II - Animals immunized with ECD-mEGF-R/VSSP-GM3/Montanide-ISA 51

Figure 3:
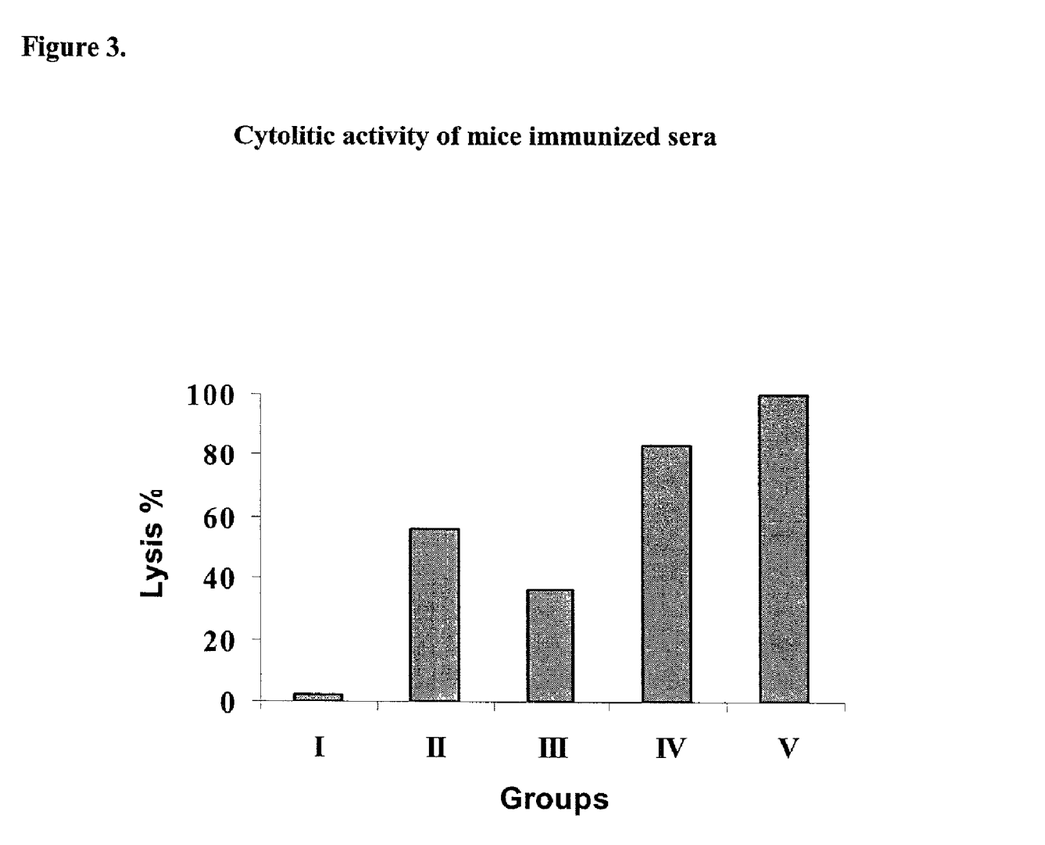
FIG. 3. Cytolytic activity of sera from mice immunized with ECD-HER-1/VSSP-GM3/IFA.

Sera from mice immunized with said vaccine composition caused 80% lysis of A431 cells expressing EGF-R, on the other hand, pre-immune sera from said mice only caused 35% lysis (FIG. 3).

Example 8

Neutralizing Ability of Sera from ECD-HER-1/VSSP-GM3/IFA Immunized Mice.

Sera from mice immunized with the vaccine composition of this invention were assayed to determine their ability to inhibit the binding of EGF to its receptor at the A431 cell membrane. To that effect, A431 cells were growth in culture plates to confluency. Once confluency was reached, an immune sera pool was added at different dilutions (1/5, 1/10, 1/20, 1/40), and then, EGF-$^{125}$I was added at a ratio of 100000 cpm/well. The volume of each well was filled up to 500 μL with PBS/1% BSA. Plates were incubated at room temperature for 1 hour, after that the reaction was quenched adding 2 mL of cold PBS/1% BSA. Thereafter the liquid in each well was removed, and wells were gently washed with PBS/1% BSA, and 300 μL of NaOH 2M were added to each well. After 30 minutes at room temperature, 200 μL were taken from each well, and the reading in a gamma-ray counter was recorded.

Figure 4:
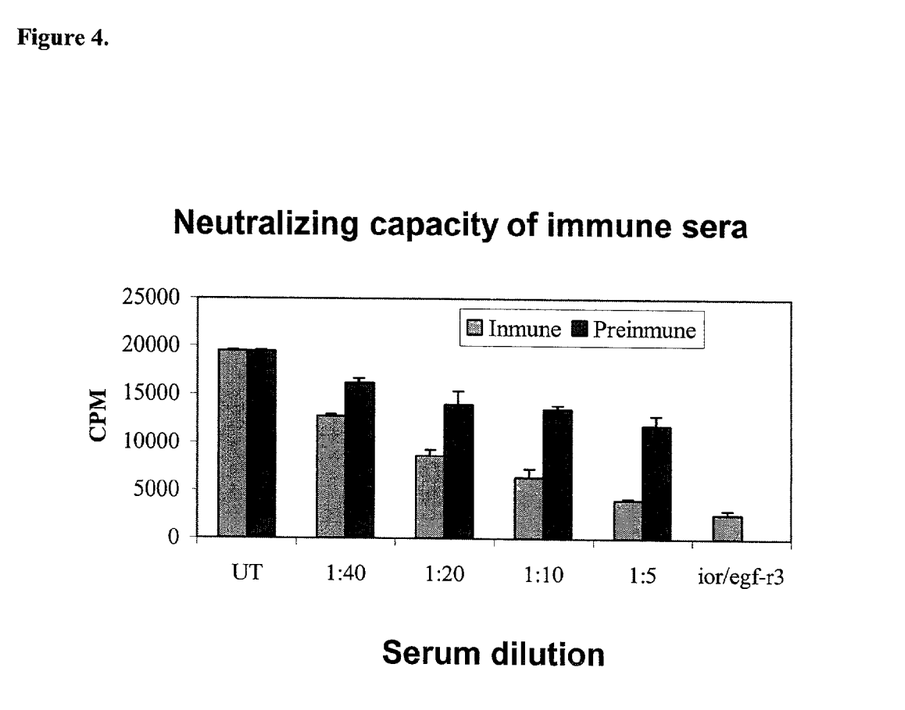
FIG. 4. Neutralizing ability of sera obtained from mice immunized with ECD-HER-1/VSSP-GM3/IFA.

The immune sera pool showed to inhibit the binding of EGF-$^{125}$I to its receptor in the A 431 cell membrane. The extent of inhibition was dependent on the sera dilution (FIG. 4).

Example 9

Life Span in ECD-HER-1/VSSP-GM3/IFA Immunized Mice.

Figure 5:
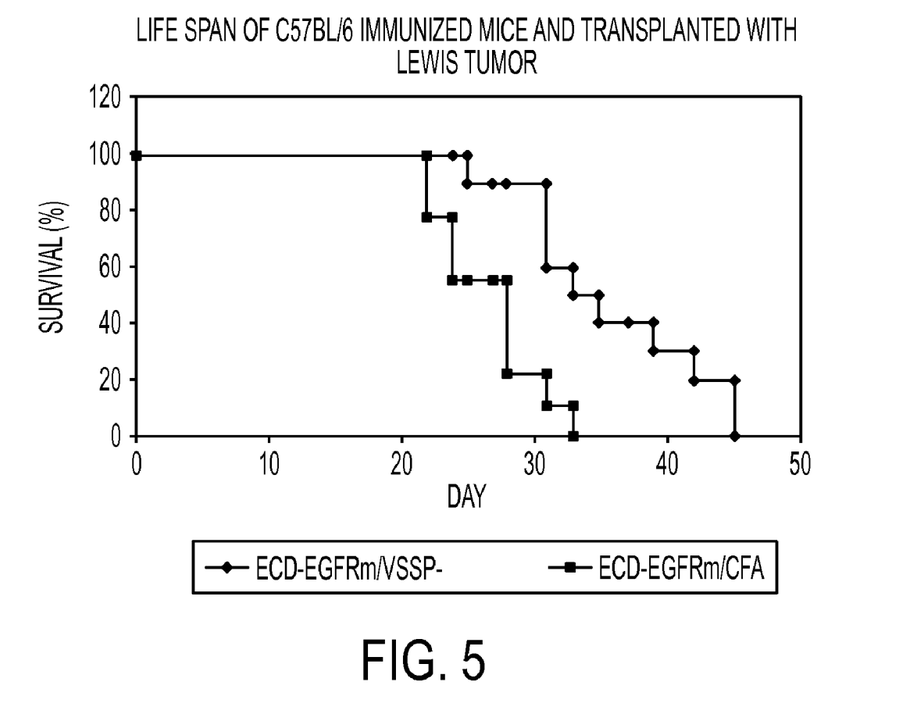
FIG. 5. Life span of mice immunized with the ECD-mEGF-R/VSSP-GM3/IFA transplanted with Lewis Tumor.

C57/BL6 line mice immunized with ECD-mEGF-R/VSSP-GM3/IFA (three 50 μg doses, every fifteen days i.m.) were inoculated i.m. with 100000 Lewis cells, and the mice were observed to determine their life span. Lewis cell are derived from a murine lung adenocarcinoma expressing EGF-R. The life span of these mice was compared to that of a group immunized with ECD-mEGF-R/CFA (three 50 μg doses every fifteen days, subcutaneously). Mice immunized with the ECD-mEGF-R/VSSP-GM3/IFA vaccine composition showed a life span significantly higher (p<0.05) than the control group (FIG. 5).

Example 10

Obtaining a Vaccine Composition Containing the P3 Chimaeric Monoclonal Antibody (P3 cMAb), VSSP(GM3), and IFA.

Proteoliposomes derived from the Outer Membrane Protein Complex from *Neisseria meningitidis* containing the GM3 [VSSP(GM3)] ganglioside, were obtained as described in Cuban Patent 130/97, and U.S. Pat. No. 6,149,921. The VSSP(GM3) were preserved at a concentration of 4.8 mg/ml in a pH 8.9 Tris/HCl solution at a temperature of 4° C., until use.

In order to prepare the immunogenic material, a solution containing 2 mg/ml of P3 Chimaeric Monoclonal Antibody (P3 cMAb) (U.S. Pat. No. 5,817,513) was mixed in a saline phosphate buffer solution with the prepared VSSP(GM3) in a ratio of 1/1 (v/v). The mixing process consisted of magnetic agitation at room temperature for 15 minutes. Afterwards, the IFA was added in a ratio of 1/1 (v/v). The pool was agitated at room temperature for 15 minutes, until the emulsion was obtained.

Another equally convenient procedure consists in mixing a solution containing 2 mg/ml of P3 cMAb in a phosphate buffer saline solution with the prepared VSSP(GM3) in a ratio of 1/1 (v/v). The mixing process was magnetic agitation at room temperature for 15 minutes, and the resulting solution was filter sterilized through 0.2 μm cellulose acetate membranes. After metering, filling in containers, and sealing processes, the preparation was preserved at 4° C. for up to one year. Just before administration to the host, the IFA preparation was added in a ratio of 1/1 (v/v), and the emulsification was obtained with agitation at room temperature for 15 minutes.

Example 11

Obtaining a Vaccine Composition Containing a Peptide from the Variable Region of the P3 cMAb Heavy Chain (CDR3NH-P3), and VSSP(GM3).

Proteoliposomes derived from the Outer Membrane Protein Complex from *Neisseria meningitidis* containing the GM3 [VSSP(GM3)] ganglioside, were obtained as described in Cuban Patent 130/97, and U.S. Pat. No. 6,149,921. The VSSP(GM3) were preserved at a concentration of 4.8 mg/ml in a pH 8.9 Tris/HCl solution at a temperature of 4° C., until use.

Just before administration to the host, the immunogenic material was prepared by first dissolving the lyophilized CDR3NH-P3 peptide in a saline phosphate buffer solution to a concentration of 4 mg/ml. Then, the solution was mixed with the VSSP(GM3) preparation in a ratio of 1/1 (v/v). The mixing process consisted in magnetic agitation at room temperature for 15 minutes.

Another equally convenient procedure consists in first dissolving the lyophilized CDR3/VH-P3 peptide in a saline phosphate buffer solution to a concentration of 4 mg/ml. Then, the solution was mixed with the VSSP(GM3) preparation in a ratio of 1/1 (v/v). The mixing process consisted in magnetic agitation at room temperature for 15 minutes, and the resulting solution was filter sterilized through 0.2 μm cellulose acetate membranes. After metering, filling in containers, and sealing processes, the preparation was preserved at 4° C. for up to one year.

Example 12

Obtaining a Vaccine Composition Containing a B16 Melanoma Oncolysate, VSSP(GM3), and IFA.

Proteoliposomes derived from the Outer Membrane Protein Complex from *Neisseria meningitidis* containing the GM3 [VSSP(GM3)] ganglioside, were obtained as described in Cuban Patent 130/97, and U.S. Pat. No. 6,149,921. The VSSP(GM3) were preserved at a concentration of 2.4 mg/ml in a pH 8.9 Tris/HCl solution at a temperature of 4° C., until use.

In order to prepare the immunogenic material, a suspension of murine melanoma B16 cell line (50×10$^6$ cells/ml) was subjected to 5 freeze/thaw cycles, alternating incubations in liquid nitrogen baths, and distilled H$_2$O baths at 37° C. The resulting cell lysate was centrifuged at 500×g for 10 minutes. The resulting pellet was re-suspended in VSSP(GM3) to a concentration of cell pellet corresponding to 10×10$^6$ cells per 2.4 mg of GM3 in VSSP. The mixture was agitated for 10 minutes at room temperature. Then, the preparation was added to the IFA in a ratio of 1/1 (v/v). The mixture was agitated at room temperature for about 15 minutes, until the emulsion was obtained.

Example 13

Obtaining a Vaccine Composition Containing Melanoma B16 Cells, VSSP(GM3), and IFA.

Proteoliposomes derived from the Outer Membrane Protein Complex from *Neisseria meningitidis* containing the GM3 [VSSP(GM3)] ganglioside were obtained as described in Cuban Patent 130/97, the U.S. Pat. No. 6,149,921. The VSSP(GM3) were preserved at a concentration of 2.4 mg/ml in a pH 8.9 Tris/HCl solution at a temperature of 4° C., until use.

In order to prepare the immunogenic material, a suspension of murine melanoma B16 cell line ($50 \times 10^6$ cells/ml) was centrifuged at 300×g for 10 minutes. The resulting pellet was re-suspended in the VSSP(GM3) to a concentration of $10 \times 10^6$ cells per 2.4 mg of GM3 in VSSP. The mixture was agitated for 10 minutes at room temperature. Then, the preparation was added to the IFA in a ratio of 1/1 (v/v). The mixture was agitated at room temperature for about 15 minutes, until the emulsion was obtained.

Example 14

Obtaining a Vaccine Composition Containing a Plasmid with the Gene Encoding the Extra-cellular Domain of Human EGF Receptor (ECD-HER-1), VSSP(GM3), and IFA.

Proteoliposomes derived from the Outer Membrane Protein Complex from *Neisseria meningitidis* containing the GM3 [VSSP(GM3)] ganglioside, were obtained as described in Cuban Patent 130/97, and U.S. Pat. No. 6,149,921. The VSSP(GM3) were preserved at a concentration of 4.8 mg/ml in a pH 8.9 Tris/HCl solution at a temperature of 4° C., until use.

The vector for inserting the DNA of interest was the pcDNA3 mammalian expression plasmid, containing the SV40 origin of replication, and the human immediate early cytomegalovirus promoter (IECP). The gene encoding the human Extra-cellular Domain of the EGF Receptor (ECD-HER-1) was inserted in this plasmid. The resulting (ECD-HER-1/pcDNA3) plasmid was used for the immunogenic preparation.

In order to prepare the immunogenic material, the ECD-HER-1/pcDNA3 plasmid solution was adjusted to a concentration of 2 mg/ml in a saline phosphate buffer solution. Then, it was mixed with the VSSP(GM3) preparation in a ratio of 1/1 (v/v). The mixing consisted in agitation at room temperature for 5 minutes. Subsequently, the preparation was added to the IFA in a ratio of 1/1 (v/v). The mixture was agitated at room temperature for about 15 minutes, until the emulsion was obtained.

Example 15

In vitro Induction of Dendritic Cells Maturation by the VSSP(GM3) Preparation

Human dendritic cells were obtained from monocytes isolated from peripheral blood, and growth for 7 days in the presence of recombinant human GM-CSF, (hr) (50 ng/ml), and hr-IL4 (1000 U/ml). On the seventh day, the obtained dendritic cells were either exposed or not, for 18 hours, to the VSSP(GM3) (1 μg/ml). As a control, dendritic cells were incubated with 0.1 μg/ml of LPS purified from *Neisseria meningitidis* strain 44/76 or with MPLA (Sigma). Each preparation's phenotype was assayed by flow cytometry.

As shown in Table 2, treatment with VSSP(GM3) caused an increment in the CD11c expression, and considerable changes in the DC CD83 maturation marker. An increase in the expression levels of the HLA-DR molecule was seen. VSSP(GM3) induced an increase in the number of cells expressing the CD86 molecule. VSSP(GM3), and LPS showed the same ability to induce maturation of treated DC. On the other hand, the detoxified variant of LPS, MPLA rated lower.

TABLE 2

In vitro induction of dendritic cells maturation by different preparations.

| | CD11c | CD86 | CD83 | HLA-DR | CD40 |
|---|---|---|---|---|---|
| Culture Medium | 37.5 | 12.5 | 5.5 | 401.5 | 9 |
| LPS | 57.1 | 35.4 | 14.6 | 672.7 | 15.8 |
| VSSP | 60 | 29.6 | 13.3 | 656.4 | 14.1 |
| MPLA | 40.1 | 15.4 | 5.6 | 415.5 | 9.7 |

Mean fluorescence intensity values, measured by FACS

Example 16

Induction of a Specific Humoral Immune Response to P3 ChimaericMAb (P3c Mab) Associated to the Administration of the Vaccine Composition.

Mice from the C57BL/6 strain were immunized with the vaccine composition referred to in Example 10. 50 μg of chimaeric monoclonal antibodies were inoculated by i.m. injection, applying 2 doses (each every 14 days). Sera samples were taken 21 days after the first immunization. As a control group, mice from the same strain were likewise immunized with the P3 cMab adjuvanted in IFA oraluminum hydroxide. Sera obtained were analyzed by ELISA techniques in order to determine the presence of anti-P3 cMAb antibodies.

100% of mice immunized with the vaccine composition as described in this invention produced higher titres of specific IgG antibodies against P3 cMAb, related to the control groups. (Table 3).

TABLE 3

Antibody response against P3c MAb induced in C57BL/6 mice inmunized with different formulations.

| Formulation | Responder animals | Specific IgG titers (mean value) |
|---|---|---|
| P3c MAb/VSSP/IFA | 5/5 | 8000 |
| P3c MAb/IFA | 4/5 | 4000 |
| P3c MAb/Alumine | 2/5 | 1000 |

Example 17

Induction of a Proliferative Cell Response Specific to CDR3NH-P3 Peptide, and Associated to the Administration of the Vaccine Composition.

Mice of the MC57BL/6 strain were immunized with the vaccine composition referred to in Example 11. 100 µg of the peptide were inoculated by i.m. injection, in 4 doses (each every 14 days). As control group, mice from the same strain were likewise immunized with CDR3/NH-P3 peptide adjuvanted in IFA or alum. Inguinal lymphatic ganglion were removed form the animals seven days after administration of the last dose, and the lymphocytes were isolated by means of organ perfusion. Lymphocytes were growth for 96 hours with the CDR3/VH-P3 peptide (50 µg/ml). During the last 18 hours of cultivation, cells were subjected to 1 µCi of tritated thymidine (Amersham, United Kingdom), and then they were harvested, and the β emissions (cpm) were detected in a scintillation counter (LKB Wallac, Finland). The cellular proliferation levels were assayed as Stimulation Index (SI). The results obtained from this assay are shown in Table4.

TABLE 4

Induction of a proliferative cell response specific to CDR3/VH-P3 peptide, in C57BL/6 mice immunized with different preparations.

|  | CDR3/VH-P3/VSSP(GM3) | CDR3/VH-P3/AIF | CDR3/VH-P3/Alúmina |
|---|---|---|---|
| 50 µg/mL | 4 ± 0.2 | 1.8 ± 0.1 | 1.6 ± 0.2 |

Stimulation index value. Notoriously, only the peptide contained in the formulation with VSSP(GM3) was capable of inducing the specific antigen proliferation.

Example 18

Induction of a Cytotoxic Cell Response Specific to ECD-mEGF-R, and Associated to the Administration of the Vaccine Composition Containing Recombinant APV, ECD-mEGF-R/APV, VSSP(GM3), and IFA.

Proteoliposomes derived from the Outer Membrane Protein Complex from *Neisseria meningitidis* containing the GM3 [VSSP(GM3)] ganglioside, were obtained as described in Cuban Patent 130/97, and U.S. Pat. No. 6,149,921. The VSSP(GM3) were preserved at a concentration of 2.4 mg/ml in a pH 8.9 Tris/HCl solution at a temperature of 4° C., until use. The viral vector for inserting the DNA of interest was the Avian Pox Virus (APV). The gene encoding the Extra-cellular Domain of the murine EGF Receptor (ECD-mEGF-R) was inserted in the APV by means of homologous recombination. The solution of ECD-mEGF-R/APV recombinant vector was adjusted to a $10^8$ pfu/ml concentration.

A VSSP(GM3) emulsion was simultaneously prepared, adding the carrier solution to IFA in a 1/1 (v/v) ratio. The mixture was agitated at room temperature for approximately 15 minutes. Subsequently, Balb/c mice were immunized IP with 200 µl of the ECD-mEGF-R/APV solution, and subsequently with 100 µl i.m. of VSSP(GM3)/IFA. The control group consisted in mice to which ECD-mEGF-R/APV, and a saline phosphate buffer solution (SPBS) was administered. Two doses were administered each every two weeks, and 21 days after commencing the experiment mice were sacrificed in order to obtain the corresponding spleen cells. CD8 T cells were isolated from the splenocytes using the magnetic pearls technology. Said T cells were stimulated during 5 days with dendritic cells derived from bone marrow (bmDC), previously pulsed with the ECD-mEGF-R immuno-dominant peptide 'NYGTNRTGL', in a ratio of 10:1 (T:bmDC), and in presence of IL-2 (50 u/ml). At the end of the stimulation, a cytotoxicity experiment was carried out, wherein the $Cr^{51}$ release was assessed when confronting different amounts of said cells to the P815 line pulsed with the 'NYGTNRTGL' peptide (Table5).

TABLE 5

Cytotoxic cell response specific to ECD-mEGF-R

| | Immunized with ECD-mEGFR/APV + VSSP(GM3) | | Immunized with ECD-mEGFR/APV + STFS | |
|---|---|---|---|---|
| | P815 + pept | P815 | P815 + pept | P815 |
| | $Cr^{51}$ release (%) | | | |
| 100:1 | 78 | 8 | 43 | 9 |
| 50:1 | 51 | 6 | 25 | 7 |
| 25:1 | 29 | 5 | 14 | 5 |

Administration of VSSP(GM3) into the animals produced a 2-fold potentiation of the induction ability of cytotoxic T cells in comparison with APV.

Example 19

Immuno-reestablishment Properties of the VSSP Vaccine Carrier

The VSSP vaccine carrier described in this invention was administered by i.m. injection to patients with metastastic melanoma in a Clinical Trial Phase I. Patients received 9 doses (200 µg of NGcGM3 in VSSP) within 6 months. The first 5 doses were administered within the first 2 months, and the 4 remaining doses were administered monthly.

At the day 0, blood was extracted from the patients (before administering the first dose), and also at day 56 (fifth dose). Simultaneously, blood was extracted from 8 healthy volunteers. The corresponding peripheral mononuclear cells (PMC) were obtained from said samples by means of the Ficoll gradient method, and the % of CD3+, CD4+ and CD8+ cells was determined by flow cytometry. As shown in Table 6, the relative expression of CD3, CD4 and CD8 T cells markers, from the PMC of 3 patients is lower than the mean expression of the healthy donors in the day 0.

Notoriously, the relative expression levels of the CD3, CD4 and CD8 T cells markers in the PMC of the same patients returned to regular levels at day 56, that is after receiving 4 VSSP(NGcGM3) injections.

TABLA 6

Expresión relativa de los marcadores de células T provenientes de las CMP de pacientes de melanoma y controles sanos. Efecto de VSSP(NGcGM3) en la normalización de los marcadores.

| | % del total de CMP Dia 0 | | | % del total de CMP Dia 56 | | |
|---|---|---|---|---|---|---|
| | CD3+ | CD4+ | CD8+ | CD3+ | CD4+ | CD8+ |
| Controles sanos | 70 | 45 | 25 | — | — | — |
| EM | 30 | 25 | 5 | 70 | 48 | 22 |
| SJ | 26 | 40 | 4 | 70 | 40 | 18 |
| VD | 15 | 28 | 4 | 70 | 56 | 20 |

BRIEF DESCRIPTION OF THE DRAWINGS

Sera from C57BL/6 mice immunized with ECD-mEGF-R/KLH/CFA (I) or ECD-mEGF-R/VSSP-GM3/IFA (II) were assayed by ELISA in order to determine the sub-class distribution of IgG induced by immunization.

A431 line cells were incubated along with pre-immune mice C57BL/6 serum (A); monoclonal antibody ior egf-r3 as a positive control (B); and immunized mice C57BL/6 serum. For immuno-detection, a second anti-mouse antibody conjugated with fluorophor, was used. The fluorescence intensity was measured in a flow cytometer.

A431 cells loaded with $^{51}Cr$ were incubated with complement and: I) Monoclonal antibody ior-t3 (against CD3, as negative control); II) Monoclonal antibody iorEGF-R-r3 (against EGF-R, as positive control); III) pre-immune serum from C57B1/6 mice; IV) serum from C57BL/6 mice immunized with ECD-HER-1/VSSP-GM3/IFA; V) an equal number of the same cells were lysated with detergents to determine the amount of total $^{51}Cr$ incorporation. The results are presented in % of specific lysis.

A431 cells were incubated in 1/5, 1/10, 1/20 and 1/40 dilutions either from a pool of sera from mice immunized with ECD-HER-1/VSSP-GM3/IFA or from a pool of pre-immune sera, at the same dilutions. EGF-$^{125}I$ (100000 com) was added to each well, and total binding was measured by incubating the cells with the EGF$^{125}I$. CPMs were measured in a gamma counter.

C57BL/6 mice immunized as described in Example 9 were transplanted with 100000 Lewis Tumor cells, and observed in order to determine the life span. The control group consisted in mice of the same strain immunized with ECD-mEGF-R/CFA, and transplanted in the same way.

The invention claimed is:

1. A pharmaceutical composition that potentiates immunogenicity of low immunogenic antigens, comprising:
   (A) one or more low immunogenic antigens selected from the group consisting of peptides, polypeptides, proteins and their corresponding nucleic acid sequences; and
   (B) an immunogenic potentiating effective amount of a vaccine carrier consisting of very small size proteoliposomes (VSSPs), wherein the VSSPs are derived from the Outer Membrane Protein Complex (OMPC) of *Neisseria meningitidis* wherein gangliosides have been incorporated into the OMPC,
   wherein the antigen is not structurally changed by chemical protein conjugation and is not incorporated into the VSSPs and wherein the vaccine carrier stimulates and potentiates both humoral and cellular immune responses against the antigen.

2. The composition of claim 1, wherein the low immunogenic antigens are growth factor receptors or their extra-cellular domains.

3. The composition of claim 2, wherein the extra-cellular domains of the growth factors receptors may or may not contain the trans-membrane region.

4. The composition of claims 2, wherein the growth factor receptors are HER-1, HER-2, PDGR-R or any variation containing the extra-cellular domain, with or without the trans-membrane region.

5. The composition of claim 4, wherein the growth factor receptor is HER-1.

6. The composition of claim 1, wherein the *Neisseria meningitidis* is either a wild type or a genetically modified strain.

7. The composition of claim 1, wherein the VSSPs are obtained by hydrophobically incorporating the gangliosides into the OMPC.

8. The composition of claim 7, wherein the gangliosides are GM1, GM3, their N-acetylated variations or their N-glycolylated variations.

9. The composition of claim 8, wherein the gangliosides are N-acetylated GM3.

10. The composition of claim 1, wherein the composition further comprises one or more adjuvants.

11. The composition of claim 10, wherein the adjuvant is an oily adjuvant, or a natural or recombinant polypeptide.

12. The composition of claim 11, wherein the oily adjuvant is the Incomplete Freund's Adjuvant.

13. The composition of claim 12, wherein the Incomplete Freund's Adjuvant is Montanide ISA 51.

* * * * *